(12) United States Patent
Kitzelmann

(10) Patent No.: US 6,248,224 B1
(45) Date of Patent: Jun. 19, 2001

(54) TOXIC SENSOR AND METHOD OF MANUFACTURE

(75) Inventor: Dieter Kitzelmann, Bonn (DE)

(73) Assignee: MST Analytics Inc., Buffalo Grove, IL (US)

( * ) Notice: Subject to any disclaimer, the term of this patent is extended or adjusted under 35 U.S.C. 154(b) by 0 days.

(21) Appl. No.: 09/310,431

(22) Filed: May 12, 1999

(51) Int. Cl.⁷ .................. G01N 27/49; G01N 27/404
(52) U.S. Cl. .................. 204/431; 204/414; 204/432; 205/780.5
(58) Field of Search .................... 204/400, 412, 204/414, 415, 431, 432, 418; 205/780.5

(56) References Cited

U.S. PATENT DOCUMENTS

| | | |
|---|---|---|
| 3,743,589 | 7/1973 | Nicholas . |
| 4,105,525 | 8/1978 | Synnott et al. . |
| 4,141,800 * | 2/1979 | Breuer et al. ................. 204/414 |
| 4,297,173 | 10/1981 | Hikuma et al. . |
| 4,394,239 * | 7/1983 | Kitzelmann et al. ............ 204/414 |
| 4,700,709 | 10/1987 | Kraig . |
| 4,851,088 * | 7/1989 | Chandrasekhar et al. ........ 204/414 |
| 5,041,204 * | 8/1991 | Kuehn et al. ................. 204/415 |
| 5,198,092 * | 3/1993 | Kiesele et al. ................ 204/402 |
| 5,234,567 | 8/1993 | Hobbs et al. . |
| 5,252,292 | 10/1993 | Hirata et al. . |
| 5,498,323 | 3/1996 | Lewenstam et al. . |
| 5,538,620 | 7/1996 | Nikolskaja . |
| 5,690,808 * | 11/1997 | Akmal et al. ................. 205/775 |

FOREIGN PATENT DOCUMENTS

| | | |
|---|---|---|
| 2 225 859 | 6/1990 | (GB) . |
| 95/22055 * | 8/1995 | (WO) . |

OTHER PUBLICATIONS

Demitras et al, "Inorganic Chemistry", ISBN:0134663594, pp. 322–324, Month Unavail., 1972.*
Article entitled "Toxic Gas CiTiceLs" from the catalog of City Technology in England. This article is undated.

* cited by examiner

Primary Examiner—Jill Warden
Assistant Examiner—Kaj K. Olsen
(74) Attorney, Agent, or Firm—Oliver A. Zitzmann; Bruce R. Mansfield

(57) ABSTRACT

An electrochemical sensor is described for the analysis of ammonia in air functioning in an amperometric measuring operation. The cell consists of either an immobilized organic electrolyte or a water based electrolyte having in both cases a dissolved $Mn^{2+}$ salt, which is immediately oxidized by an electrochemical process at a measuring electrode of the cell to $Mn^{4+}$ ion, if a pH-shift of the electrolyte in the presence of ammonia takes place. The sensor consists of three electrodes comprising a catalytic active carbon measuring electrode, a second carbon auxiliary electrode (counter electrode) in contact with the electrolyte and a third electrode in contact with the electrolyte, which acts as reference electrode. The sensor can be used for ammonia over a wide range and can be adapted for other uses, such as volatile amines.

17 Claims, 2 Drawing Sheets

TOXIC SENSOR AND METHOD OF MANUFACTURE

BACKGROUND OF THE INVENTION

1. Field of the Invention

The present invention pertains to sensors such as for toxic compounds in gases or fluids and, in particular, to the manufacture and use of a detector for sensing ammonia.

2. Description of the Related Art

Toxic gas sensors are relied upon to an ever increasing extent to safeguard the health and safety of personnel entering a possibly hazardous area. With added attention being directed to worker's safety in confined spaces, there is a need for rapidly identifying gaseous or liquid agents, which (even if not asphyxiating or combustible) are nonetheless toxic, using compact, portable equipment. With an increasing integration of electronics, the ability to obtain an instrument read-out of toxic sensors is becoming simpler. However, there remains a need to provide sensors having improved accuracy and sensitivity to avoid inappropriate conclusions drawn from a sensor's output indication.

Electrochemical methods are frequently used for analyzing traces of gases. In methods of this kind, the measuring electrode of a galvanic cell is brought into contact with the gas to be examined, producing an electrical current which is proportional to the concentration of the compound to be measured. In the case where reducible gases (for example, oxygen, nitrogen dioxide, ozone or chlorine) is measured, there is a reaction on a measuring electrode which acts as a cathode, while oxidizable gases (for example, hydrogen sulfide, carbon monoxide, hydrogen) react on a measuring electrode acting as an anode.

Many electrochemical ammonia sensor cells in use today employ the Sevringhaus (potentiometric) Principle (DS-A-2009937). A pH glass electrode is employed as a measuring electrode, and the potentials between the pH electrode and a reference electrode are measured. The difference in potential serves as a measurement signal, related to the presence of ammonia through a pH-shift of the electrolyte according to the reaction $NH_3+H_2O \rightarrow NH_4^+ + OH^-$. This process suffers drawbacks in that the signal is logarithmically related to the ammonia concentration. Moreover, the time to fix the balance is extremely slow. Further, other gases (e.g., $SO_2$, HCl, $CO_2$) are able to change the pH-value of the electrolyte, falsifying the measurements.

Other commercially available ammonia sensors (such as those available from Sensoric GmBH & Co., operate on the amperometric principle. Sensors of this type respond to a direct transformation of ammonia passing through a gas-permeable membrane onto a catalytic working measurement electrode, according to the following equation:

$$NH_3 \rightarrow N_2 + 6H^+ + 6e$$

Electrodes in these types of sensors include measure, reference and counter-electrodes in contact with a water-free organic gel electrolyte, cooperating with the electro catalyst to oxidize the ammonia to nitrogen. It is important for direct transformation that the electrolyte be a water-free medium. One example of a highly effective catalyst is platinum black. The reaction causes an electric current that is proportional to the concentration of ammonia in the measuring gas. Unfortunately, the oxidation rate of ammonia to nitrogen is not fast enough at higher concentrations, and intermediate by-products of the oxidation of ammonia causes the measuring electrodes to become partly blocked, resulting in a temporary poisoning of this electrode, with a continuous decline in the measuring signal if the ammonia gas is not withdrawn from the sensor. Furthermore, the selectivity of this sensor is not very high.

Another type of amperometric measurement procedure is known from GB 2,225,859. The ammonia passes a gas-permeable membrane into an electrolyte containing soluble non-oxidizable reagent. The reagent changes through a reaction with ammonia to a substance that is electrochemically oxidizable, preferably an organic ammonium salt such as hydrochloride of Tris(hydroxymethyl)-aminomethane ("Tris-HCl"). This transforms the ammonium salt into Tris(hydroxymethyl)-aminomethane, which is oxidized in a second stage, in place of the ammonia itself on the measuring electrode. A highly effective catalyst, either rhodium or gold, must be used with this procedure to produce oxidation of the newly formed amine. Unfortunately, other substances, such as by-products in the measuring gas (e.g., CO or alcohol) will also be measured. Another disadvantage is that a bias-potential is necessary to cause a reaction. This causes long warm-up periods, dependable on temperature, degrading the measuring behavior of the sensors, and impairing the ability to obtain a favorable zero-noise level. In this type of procedure, ammonia reacts only with a particular substance (Tris-HCl) added to the electrolyte, producing an electrochemical active species which later transforms itself at a measuring electrode, creating a measurement signal proportional to ammonia concentration.

A similar measuring procedure is known (U.S. Pat. No. 5,234,567) which uses a chemical species which reacts with ammonia to form a product which is more electrochemically active than ammonia. The chemical species is one of iodine or Nesslers reagent or a solution of manganese and silver nitrate. The preferred chemical reagent is iodine. The ammonia diffuses into the sensor and dissolves readily in water to product $OH^-$ (reaction 1), which is necessary for a secondary reaction forming iodine-ions (reaction 2).

$$NH_3 + H_2O \rightarrow NH_4^+ + OH^- \tag{1}$$

$$6OH^- + 3I_2 \rightarrow 5I^- + IO_3^- + 3H_2O \tag{2}$$

$$2I^- \rightarrow I_2 + 2e \tag{3}$$

The measuring signal results from the reformation of iodine from the iodine-ion (reaction 3). This must occur at an elevated potential of the measuring electrode. A +300 mV bias potential is required between the reference and measuring electrodes. This requires a long warm up time to stabilize the zero reading of the sensor. Another disadvantage is that a very small side reaction can also form iodine-ions from iodine (reaction 4).

$$I_2 + 3H_2O \rightarrow 5I^- + IO_3^- + 6H^+ \tag{4}$$

This side reaction is temperature dependent with a small increase of temperature substantially increasing the zero current, which again is a big disadvantage.

SUMMARY OF THE INVENTION

An object of the present invention is to provide an electrochemical sensor for the analysis of gaseous and liquid ammonia and volatile amines.

A further object of the present invention is to provide an ammonia sensor having improved accuracy over its designated operating range.

Yet another object of the present invention is to provide a sensor which is relatively free of maintenance requirements, and which remains stable over extended periods of time.

It is an object of the present invention to provide a sensor for ammonia and its derivatives which does not require a bias potential and which has a stable zero-noise level despite fluctuating ambient temperatures and humidity. It is also an object of the present invention to provide a sensor of this type which is able to measure elevated ammonia concentrations over extended periods of time.

It is important that the sensor provide relatively rapid determinations of toxic concentrations, and do so simply without requiring complex external equipment.

These and other objects of the present invention are provided in a sensor effective for measuring a target component in a gaseous or aqueous samples, the sensor comprising:

a housing containing an electrolyte, the electrolyte including a stable oxidizable metal ion;

a measuring electrode in contact with said electrolyte, the measuring electrode including a support layer and a catalyst effective for catalyzing the oxidation of said stable oxidizable metal ion in the presence of said target component; and a counter electrode in contact with said electrolyte.

DETAILED DESCRIPTION OF THE PREFERRED EMBODIMENT

Figure 1:
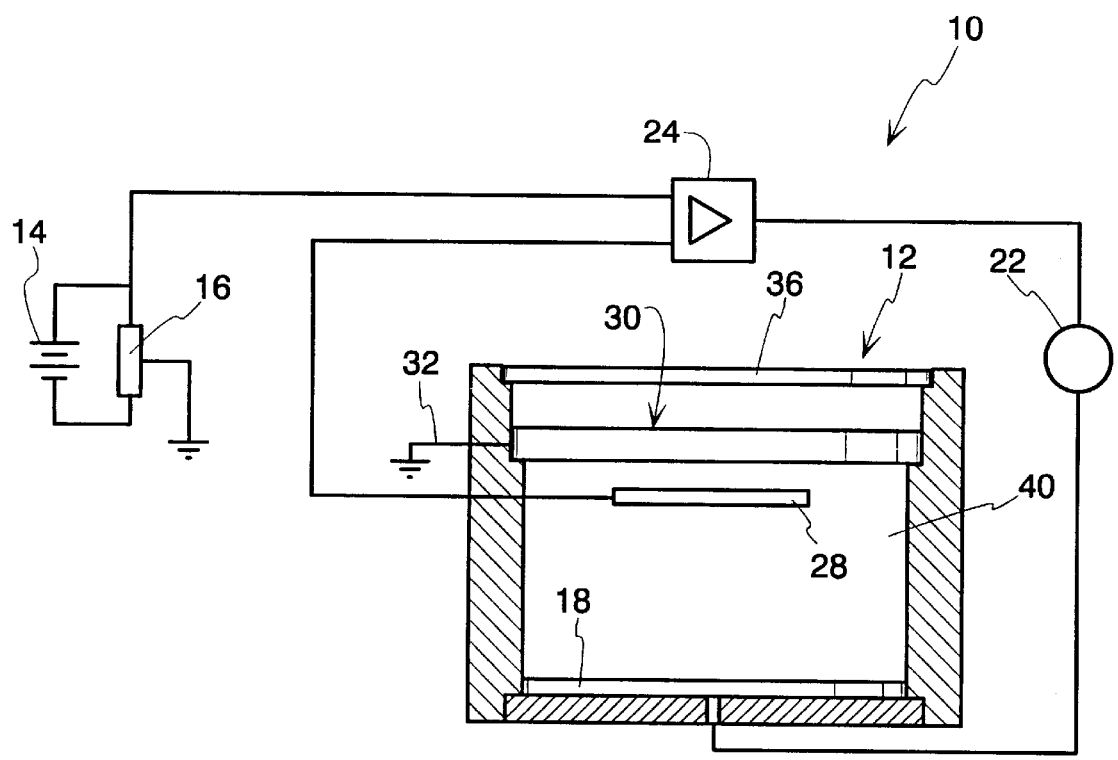
FIG. 1 shows a schematic view of a sensor according to the principles of the present invention.

Referring now to the drawings, and initially to FIG. 1, a toxic gas sensor system is generally indicated at 10. Included are a sensor generally indicated at 12 and associated external circuitry equipment comprising a battery 14 and a conventional bias voltage adjustment circuit 16 which apply an impressed voltage between the reference electrode 28 and the measuring electrode 30. An output device 22 monitors the current flow into the sensor 12. The sensor is employed to measure concentrations of gaseous and liquid target materials, such as ammonia and volatile amines.

A potentiostat circuit applies a control voltage between reference electrode 28 and the sensing electrode. A sensing or measuring electrode generally indicated at 30 is grounded at 32, and is located immediately adjacent a diffusion barrier 90. The diffusion barrier preferably comprises a porous membrane of conventional polytetrafluoroethylene material. As will be seen herein, the diffusion barrier is preferably in intimate contact with the measuring electrode 30 so as to improve measuring accuracy and response time for the system.

The sensor 12 operates on the amperometric basis. The reference electrode 28 serves as an electrical reference point which, in combination with an external electronic voltage stabilizing circuit 24 holds the potential of the measuring electrode 30 constant.

Preferably, the reference electrode 28 employs Ruthenium as catalyst, overlaid on a perforated tape substrate, preferably of polytetrafluoroethylene material. The ruthenium catalyst has been found to provide an optimal working potential for measuring electrode 30 when employed with the preferred electrolyte 40.

Figure 2:
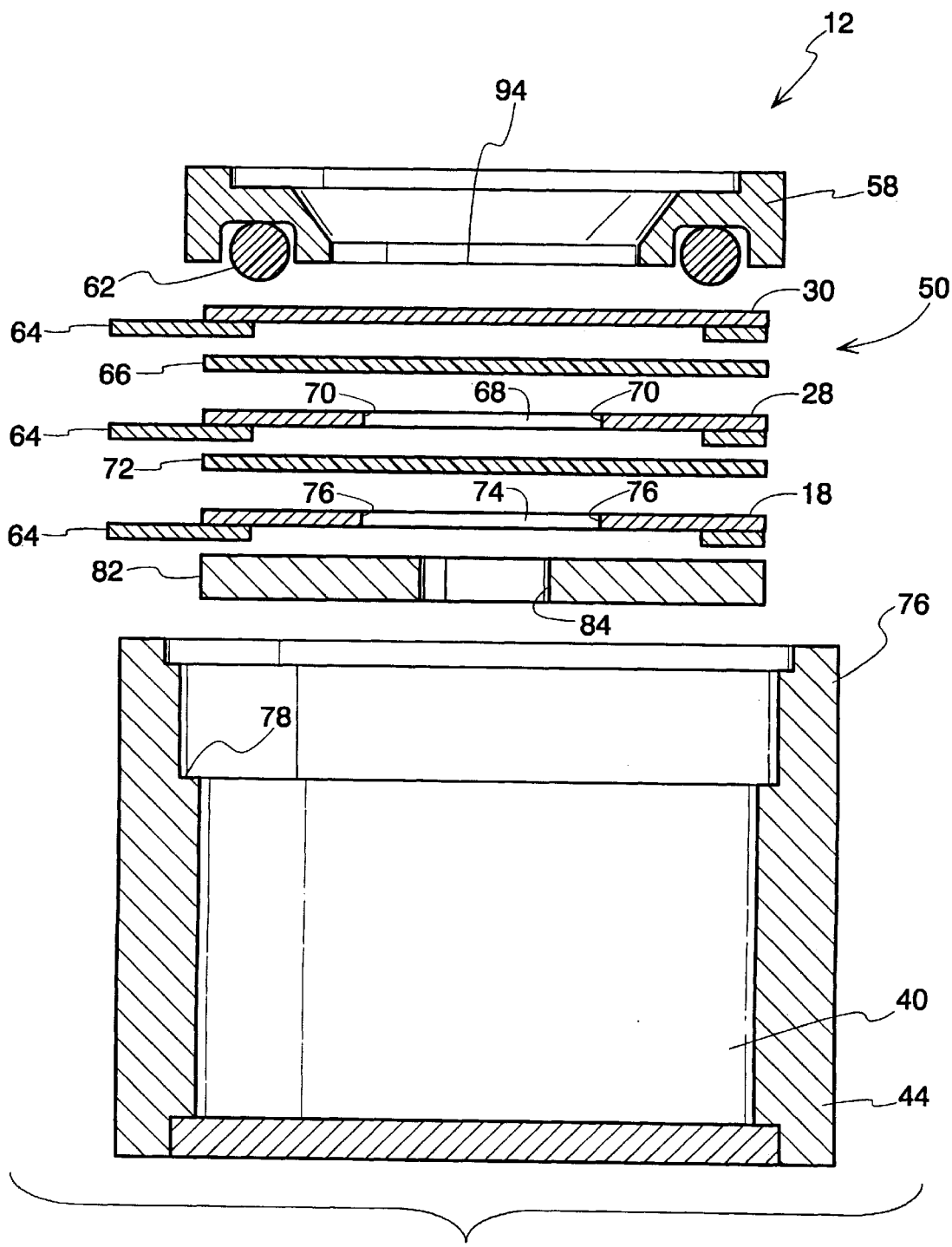
FIG. 2 is a fragmentary exploded view thereof.

The physical construction of sensor 12 will now be discussed with additional reference to FIG. 2. Sensor 12 includes a housing 44 formed of any suitable material resistant to the electrolyte 40. Preferably, housing 44 is constructed of ABS plastic or polyester material. As will be seen herein, the internal cavity of housing 44 is sealed at the top by an electrode assembly generally indicated at 50. Entrance to the cavity of housing 44 is gained by removing bottom cover 52, which is hermetically sealed to housing 44 after the electrolyte has been added. Ultrasonic welding or another conventional mode of sealing is contemplated, and it is generally preferred that the resulting construction be liquid-tight.

The electrolyte 40 may include virtually any suitable organic or water based electrolyte compatible with the reagents employed. In this aspect of the invention, the electrolyte includes a stable oxidizable metal ion. As used herein, the term "stable oxidizable metal ion" refers to metal ions which remain at a given oxidation state under standard conditions. Metal ions useful in the present invention may be oxidized to a higher oxidation state under the appropriate conditions, such as for example, exposure of the sensor to a target component in the presence of a catalyst, and are effective for providing ionic conductivity. The metal ion that is used is a manganese-ion, which stably exists as $Mn^{+2}$ and is oxidized to $Mn^{+4}$.

The stable oxidizable metal ion is provided to the electrolyte in the form of a salt. The stable oxidizable metal salts may be any salt which is soluble in the organic or water based electrolyte and which is effective for providing ionic conductivity. The electrolyte preferably comprises a hydrous solution of manganese (II) salt and most preferably, manganese (II) nitrate or manganese (II) sulfate.

The stable oxidizable metal salt may be provided in a concentrated form and diluted in water or organic solvent to provide the electrolyte. In the case of an organic solvent, propylene carbonate and/or butyrolactone may be used as a solvent for the oxidizable metal salt.

The reference electrode 28 in combination with the potentiostat 24 keeps the potential of the measuring electrode constant by applying an electrical current. The measured current indicated by output device 22 exhibits a linear dependence to the concentration of the target material, herein ammonia, particularly gaseous ammonia, and volatile amines. Volatile amines that can be detected and measured by the present invention include methylamine and tertiary-butylamine.

Referring again to FIG. 2, the electrode package 50 includes a holding ring 58, including an O-ring of VITON or other suitable material, indicated by the reference numeral 62. The measuring electrode 30 is located underneath the holding ring 58 and is in electrical contact at its bottom surface with a first of three collecting electrode 64. A first insulator layer or separator 66 is made of suitable dielectric material, and preferably comprises a glass fiber fleece. Separator 66 prevents direct electrical contact between the measuring electrode 30 and the reference electrode 28.

Reference electrode 28 preferably has an annular shape with a central opening 68 identified by reference lines 70, shown for clarity of illustration. A second separator 72 prevents direct electrical contact between the reference electrode 28 and the lowermost counter electrode 18. Preferably, counter electrode 18 has the same general dimensions and shape of annular reference electrode 28. Accordingly, counter electrode 18 includes a central opening 74, the dimensions of which are illustrated by reference lines 77. An optional support disk 82 provides support for the relatively thin flexible electrode and separator layers disposed thereabove. As can be seen in FIG. 2, the upper end 76 of housing 44 includes a pocket or recess 78 which receives the support 82. The disk-shaped support 82 includes a central opening 84 to allow the passage of electrolyte 40 therethrough.

Figure 3:
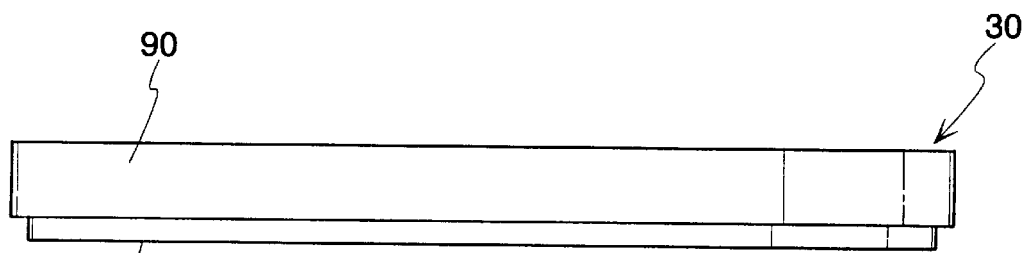
FIG. 3 is an elevational view of a measuring electrode component thereof.

With additional reference to FIG. 3, the measuring electrode includes a support layer, preferably a perforated support tape 90, joined in intimate contact with a catalyst layer 92. Preferably, the support layer 90 comprises conventional polytetrafluoroethylene tape having a thickness of about 0.1 mm to about 0.5 mm, a pore size of about 20% to about 50%, and having about $0.1\mu$ to about $1\mu$ of pore diameter. The catalyst layer 92 may be formed from a variety of materials, including gold powder, graphite powder or graphite felt and mixtures thereof. Preferably, measuring electrode 30 is prepared by mixing a gold powder or a finely dispersed graphite powder with a tetrafluoroethylene dispersion to form a wet mixture which is then applied to the porous support tape 90. The catalyst preferably is applied at a rate of 5 to 10 mg/cm$^2$.

The catalyst layer is dried on the polytetrafluoroethylene tape 90 and is thereafter pressed and sintered in order to obtain a strong intimate bond on a microscopic basis, between the tape and catalyst layers. While gold powder and graphite powder are preferred, other materials can be chosen as a catalyst for the oxidation of manganese (II) to manganese (IV). Examples of alternative measuring electrode catalysts include iridium and ruthenium.

As will be appreciated from the above, an inexpensive construction of the sensor 12 is possible. As a further advantage, no special additional treatment, such as activation of the catalyst layer or the porous support has been found to be necessary.

Figure 4:
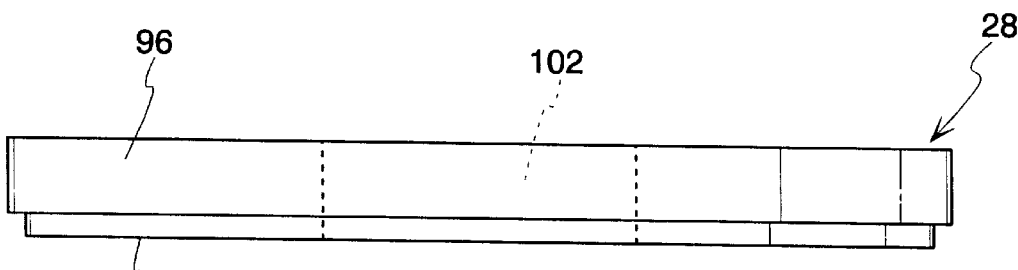
FIG. 4 is an elevational view of a ring electrode therefor.

Referring now to FIG. 4, the reference electrode 28 has an overall ring or annular shape with a central aperture 102, and employs a construction similar to that of the measuring electrode 30. Preferably, reference electrode 28 comprises a tape support 96, preferably of polytetrafluoroethylene material. A catalyst, preferably of Ruthenium Black is formed as a wet mixture with tetrafluoroethylene. This mixture is then applied to the perforated tape support 96 and allowed to dry. Preferably, the support layer 96 and catalyst layer 98 are pressed together and sintered to form an intimate bond between the two. The pressing and the sintering of the reference electrode is not as critical as for the measuring electrode and may be substituted by other conventional electrode construction techniques.

Referring again to FIG. 2, it can be seen that the electrolyte 40 within the cavity of housing 44 can freely travel in an upward direction so as to contact the underneath surface of measuring electrode 30. The electrolyte travels through central opening 84 in disk layer 82 and the separator layers 66, 72 are constructed so as to be readily permeable to the electrolyte. Accordingly, the electrolyte travels through the central openings 74 and 68 of electrodes 18 and 28, passing through the final separator layer 66 so as to come into contact with the counter-reference or measuring electrode 30.

The holding ring 58 maintains the sandwich or nested construction of the electrode assembly 50 by applying a compressive force thereto, pressing the stack of assorted layers against the recess or pocket surface 78 of housing 44. The O-ring 62 provides an environmental seal for the end edges of the electrode assembly and further is readily deformable under pressure to prevent damage to the underlying layers as the compressing force is applied, thus greatly reducing the skill and attention needed to construct the sensor 12.

The holding ring 58 may be joined to any suitable structure for bringing the target material, either fluid or gas, in contact with the upper surface of measuring electrode 30. With reference to FIGS. 2 and 3, the support tape 90 of measuring electrode 30 serves several functions which cooperate together for the successful operation of the sensor 12. As mentioned, the upper surface of the measuring electrode 30 is in contact with the target material. Preferably, the upper surface of electrode 30 comprises the support tape 90 shown in FIG. 3, and this support tape is constructed so as to be permeable to the target gas, allowing its downward passage into contact with the underlying catalyst layer 92. Preferably, as mentioned, the catalyst layer 92 is pressed, sintered and otherwise intimately bonded to the support tape 90. The perforated support tape 90 will, to some extent, function as a collimator, the pathways of which are physically terminated at their lower extent at the point of intimate contact with the catalyst layer 92. This construction is believed to contribute to the desired reactivity of the catalyst and, in addition, provides an optimally short transit length for the target gas. An important feature of the present invention is the diffusion barrier joined to the measuring electrode catalyst to form a unitary intimately bonded construction. The diffusion barrier limits the flow of target gas to the catalyst of the sensing electrode and is preferably located immediately adjacent the catalyst so that all of the target gas reaching the catalyst is allowed to fully react with the electrolyte, causing an increase of OH$^-$-ions, so that the oxidation of Mn$^{2+}$ at the measuring electrode catalyst can occur. These features are, in part, believed to be important for the relationship between the output current signal of the sensor and the partial pressure of the target gas.

Further, as mentioned, the bottom surface of electrode 30, i.e., the bottom surface of catalytic layer 92 (see FIG. 3) is in contact with the electrolyte which is allowed to travel from the cavity of housing 44. As a result, the bottom portion of the catalyst layer 92 is penetrated by the electrolyte so as to form a three-phase boundary of the electrolyte, the catalyst, and the target gas, the site of an electrochemical reaction of improved sensitivity and response time. The electrochemical reaction in this case is an indirect process where a precursor chemical reaction takes place before a following electrochemical reaction is allowed to occur.

The electrochemical reaction at the three-phase boundary results in a measurement current (indicated by output device 22) which exhibits an improved linear dependence with respect to the concentration of target gas, and an extremely stable zero-noise level in the absence of target gas, even with fluctuating ambient temperatures. Further, the sensor of the present invention has been found to be capable of measuring elevated target gas concentrations over prolonged periods of time.

As mentioned, the target gas is transported by a diffusion layer of the measuring electrode to the three-phase boundary located at the measuring electrode catalyst layer. This results in an immediate increase of OH$^-$ concentration according to the formula $NH_3+H_2O \rightarrow NH_4^+ +OH^-$. With activity of the catalyst layer, an electrochemical oxidation of manganese (II) to manganese (IV) result. This oxidation reaction, where $Mn^{2+}+2H_2O \rightarrow MnO_2+4H^++2e$ is enabled because H$^+$ ions represented in the equation are neutralized with OH$^-$ ions to form water. As a result, commercial sensors constructed according to principles of the present invention have been found to exhibit improved performance, delivering a linear signal for ammonia concentrations ranging between 0 and 100 ppm, with the reaction time to ammonia taking between 30 and 60 seconds. Typically, commercial sensors deliver an output signal of 80 to 160 nA/ppm.

As set out above, the sensor according to the principles of the present invention operates on an amperometric basis in a three electrode mode. The preferred reagent introduced into the electrolyte comprises a substance which cannot be oxidized in the absence of ammonia, either through oxygen or through an electrochemical reaction. The reagent employed in the present invention is allowed to oxidize only after an increase of the pH value of the electrolyte in the presence of ammonia. As mentioned, the preferred reagent comprises a manganese (II) salt in an aqueous solution or an organic solvent such as propylene carbonate. As a result, the electrochemical reaction occurs at a faster rate than the chemical oxidation of manganese (II) salt with oxygen present in the air. The use of manganese (II) salt in higher concentrations, preferably as nitrate, sulfate or chloride, suppresses evaporation of water of an aqueous electrolyte, while providing sufficient capacity to measure even elevated levels of ammonia concentrations over long periods of time, during which the manganese (II) will be consumed.

The measuring electrode can be formed with a porous layer of carbon felt covered with a porous hydrophobic polytetrafluoroethylene membrane. The ammonia or its derivatives being measured is diffused through the porous membrane to the electrode and is dissolved in the electrolyte (either aqueous or organic) trapped in the measuring electrode catalyst, causing an increase of $OH^-$ ions according to the equation $NH_3 + H_2O \rightarrow NH_4^+ + OH^-$.

As determined by Allen J. Baro, of Marcel Dekker, Inc. in an article entitled "Standard Potential In Aqueous Solution", the pH dependence of the standard potential for the oxidation of manganese (II) salt is given by the equation $$Mn^{2+} + 2H_2O \rightarrow MnO_2 + 4H^+ + 2e (E^0 = 1.23 \text{ V}).$$

With a pH-shift, a potential shift in a more negative direction occurs with an immediate electrochemical oxidation to manganese (IV) occurring at the porous measuring electrode. A theoretical, much slower oxidation of manganese (II) through oxygen of the air can occur, if at all, only on an insignificant level. The potential for the measuring electrode is fixed by the reference electrode which preferably contains a thinly distributed layer of novel metal catalysts. It is unlikely that mangan-hexamin $[Mn(NH_3)_6]^{++}$ complex salt will be formed because the affinity of ammonia to water is greater than the affinity of ammonia to manganese (II) ion and only traces of ammonia ion are present in the electrolyte. Because the formation of $[Mn(NH_3)_6]^{++}$ ions requires very high $NH_4^-$ ion concentrations, manganese (II) is allowed to oxidize due to a pH-shift of the electrolyte. Advantageously, the manganese (II) salt exhibits a very low pH buffer capacity, further enabling a pH-shift in the presence of ammonia.

At the other end of the electrode stack, the counter electrode 18 acts to balance out the reaction at the measuring electrode 30 by reducing oxygen to water according to the following equation $$O_2 + 2H_2O + 4e \rightarrow 4OH^-.$$

Further advantages of the present invention will become apparent from consideration of the following examples.

EXAMPLE 1

In a first example, a three electrode sensor is employed with the measuring electrode 30 of gold catalyst construction, reference electrode 28 of ruthenium catalyst construction and a counter electrode 18 of graphite layer construction. The central gas aperture 94 of holding ring 58 (see FIG. 2) is constructed with a central diameter of 7 millimeters. The electrolyte was formed from a 40% solution of 10 manganese nitrate in water. Approximately 0.5 ml was filled in the cavity of housing 44, leaving a small portion of the cavity unfilled to accommodate any gaseous $H_2O$ which may be diffused into the sensor should the hydrous electrolyte become diluted by an elevated humidity level in the ambient atmosphere. After filling with the electrolyte, the bottom of housing 44 is hermetically sealed with ultrasonic welding of bottom cover 52. The housing is constructed of ABS plastic. The potential difference between the measuring and reference electrodes was adjusted to zero, with the zero current measuring less than 50 nA over a waiting period of several minutes. The sensor was then exposed to 100 ppm ammonia in air, with the measuring signal at 22 being increased to 13.5 microamperes within 60 seconds. The response time rose to 90% of the final sensitivity in less than 30 seconds. As soon as the sensor was exposed to fresh air, the measuring signal at 22 fell to the original zero level value within 60 seconds. Injections with 100 ppm ammonia were repeated several times resulting in precise near identical values. Virtually no cross sensitivity was recognized when the sensor was exposed to 300 ppm CO, 1000 ppm $H_2$, 1200 ppm methanol or 500 ppm $CO_2$.

EXAMPLE 2

In a second example, the measuring electrode was comprised of finely dispersed graphite powder, a similar construction being employed for the counter electrode 18. The reference electrode 28 was the same as in Example 1. The electrolyte employed provides a solution of 20 weight percent manganese (II) sulfate in water. Again, 0.5 milliliter was added to the housing cavity, with the bottom cover 52 thereafter being ultrasonically welded to the ABS housing. A zero current of 85 nA was observed after a few minutes. Upon exposing the sensor to 100 ppm ammonia in air, a measuring signal of 15.4 microamperes was observed at output 22 after a waiting period of 60 seconds. Upon removal of the ammonia/air mixture and exposing the sensor to fresh air, the output value dropped to its original level within 60 seconds. The same measuring sensitivity was observed upon repeated cyclic exposures of the sensor.

EXAMPLE 3

Again a three electrode sensor was employed, with the measuring, reference and counter electrodes remaining the same as in Example 2. In the third example an electrolyte solution was formed of 0.5 ml of 10% manganese (II) nitrate solution in propylene carbonate. To form a gel structure of the electrolyte 0.1 g of a polymethylmethacrylate powder with a particle size of 150 μm was added. The housing 44 in bottom cover 52 was formed of polytherephthalate. A zero current level of 38 nA was observed over a waiting period of 2 hours. Upon exposure of the sensor to a gas sample comprising 100 ppm ammonia in air, the measuring signal at 22 was observed to be 9.5 microamperes. Upon repeated tests, the sensor of Example 3 showed an observable zero current shift attributed to sudden changes in the humidity of the air carrying the ammonia target material.

As can be seen from the above, the present invention provides an improved sensor for the control of ammonia or its derivatives, such as volatile amines in the surrounding air, as well as for the determination of ammonia in liquids. The sensor exhibits exceptional selectivity and an extremely stable zero-noise level even with fluctuating ambient temperatures. In addition, the sensor will work without bias potential and the reference electrode and its associated external circuitry can be omitted, if desired. In addition, the sensor according to principles of the present invention measures higher ammonia concentrations over extended periods of time.

Certain variations are possible. For example, the electrolyte can be gelled using conventional techniques. It is important, however, that the separator layer be readily porous to the gel material.

Further, although examples of operation are given for air sensors according to the present invention can be readily employed to measure ammonia and its derivatives as well as gaseous phases in a liquid environment. The only procedures for liquid samples is to add, for example, NaOH to the sample to increase the pH of this sample to pH of >9. This is necessary to form $NH_3$ from $NH_4^+$ ions. Further, although it is preferred that the support layer for the catalyst function as a diffusion barrier, it is possible to practice the present invention with the diffusion barrier being spaced from the catalyst. It is also possible that several diffusion barriers be employed in conjunction with the catalyst layer, either in intimate bonding therewith or in a spaced part arrangement.

The drawings and the foregoing descriptions are not intended to represent the only forms of the invention in regard to the details of its construction and manner of operation. Changes in form and in the proportion of parts, as well as the substitution of equivalents, are contemplated as circumstances may suggest or render expedient; and although specific terms have been employed, they are intended in a generic and descriptive sense only and not for the purposes of limitation, the scope of the invention being delineated by the following claims.

What is claimed is:

1. A sensor effective for measuring a target component in a gaseous or aqueous samples, the sensor comprising:
    a housing containing an electrolyte, the electrolyte including an oxidizable manganese ion;
    a measuring electrode in contact with said electrolyte, the measuring electrode including a support layer and a catalyst effective for catalyzing the oxidation of said oxidizable manganese ion the presence of said target component; and
    a counter electrode in contact with said electrolyte.

2. A sensor according to claim 1 wherein the oxidizable manganese ion is $Mn^{+2}$.

3. A sensor according to claim 2 wherein the catalyst is effective from catalyzing the oxidation of $Mn^{+2}$ to $Mn^{+4}$.

4. A sensor according to claim 3 wherein the oxidizable manganese ion is provided as a salt selected from the group consisting of manganese (II) nitrate, manganese (II) sulfate, manganese (II) chloride and mixtures thereof.

5. A sensor according to claim 1 wherein the support layer is polytetrafluoroethylene.

6. A sensor according to claim 1 wherein the catalyst is selected from the group consisting of gold powder, graphite powder or graphite felt and mixtures thereof.

7. A sensor according to claim 1 wherein the catalyst is bonded to the support layer.

8. A sensor according to claim 1 wherein the target component is ammonia or volatile amine.

9. A sensor according to claim 1 wherein the counter electrode is effective for reducing oxygen to water.

10. In an electrochemical detector on the amperometric basis for the detection of ammonia or volatile amines in gaseous or liquid environments, the electrochemical detector having a catalytic active measuring electrode exposed to the ambient air or ambient liquid and communicating through an electrolyte chamber with a counter electrode and a reference electrode, wherein the electrolyte chamber includes an electrolyte and the electrolyte is an organic electrolyte immobilized in form of a gel and wherein the electrolyte contains a salt of an oxidizable manganese ion which is soluble in this gel and which is able to convert into a species of a higher oxidation level by an electrochemical oxidation process at the measuring electrode due to the presence of ammonia or volatile amines.

11. In the electrochemical detector according to claim 10, wherein the salt is a $manganese^{2+}$-salt in an organic gel electrolyte.

12. In the electrochemical detector according to claim 11, wherein the salt is manganese (II) nitrate.

13. In the electrochemical detector according to claim 10, wherein electrolyte further comprises propylene carbonate.

14. In the electrochemical detector according to claim 10, wherein the gel comprises propylene carbonate, the $manganese^{2+}$-salt and polymethylmethacrylate as polymer.

15. In the electrochemical detector according to claim 10, wherein the measuring and/or counter electrode consists of carbon cloth or carbon fleece.

16. In the electrochemical detector according to claims 10, wherein the reference electrode contains a mixture of ruthenium powder and a hydrophobic binder.

17. A sensor for a target component of a fluid, comprising an electrochemical cell which includes:
    a housing;
    an electrolyte in the housing, wherein the electrolyte includes an oxidizable manganese ion;
    a counter electrode in the housing in contact with said electrolyte;
    a measuring electrode in the housing in contact with said electrolyte;
    wherein the measuring electrode comprises:
        a support layer in contact with said target component;
        a catalyst layer in contact with said electrolyte, said catalyst layer carried on the support layer and said catalyst effective for catalyzing the oxidation of said oxidizable manganese ion the presence of said target component, wherein said oxidation results in a charge flow which is related to a concentration of the target component; and
        said support layer comprising a diffusion barrier in intimate contact with the catalyst layer, said diffusion barrier effective for providing an impervious barrier to said electrolyte.

* * * * *